United States Patent [19]
Taniguchi et al.

[11] Patent Number: 4,582,944
[45] Date of Patent: Apr. 15, 1986

[54] PROCESS FOR PRODUCING HYDROXYDIPHENYL ETHERS

[75] Inventors: Katsuo Taniguchi, Iwakuni; Hideo Nakamura; Terunori Fujita, both of Ohtake, all of Japan

[73] Assignee: Mitsui Petrochemical Industries, Ltd., Tokyo, Japan

[21] Appl. No.: 606,611

[22] Filed: May 3, 1984

[30] Foreign Application Priority Data

May 10, 1983 [JP] Japan ................................. 58-80142

[51] Int. Cl.$^4$ ............................................. C07C 41/09
[52] U.S. Cl. ..................................... 568/637; 568/638
[58] Field of Search ........................ 568/638, 637, 698

[56] References Cited

U.S. PATENT DOCUMENTS 2,739,171 3/1956 Linn ..................................... 568/638
3,886,218 5/1975 Biller et al. ......................... 568/638

Primary Examiner—Bernard Helfin
Attorney, Agent, or Firm—Sherman and Shalloway

[57] ABSTRACT

A process for producing a hydroxydiphenyl ether, which comprises reacting at least one hydroquinone compound with itself or with a monohydric phenol compound in the presence of a catalyst composed essentially of a synthetic mica in which at least 10 mole % of cation-exchangeable interlayer cations are made up of a metal ion other than alkali metal ions, and/or a proton.

11 Claims, No Drawings

PROCESS FOR PRODUCING HYDROXYDIPHENYL ETHERS

This invention relates to a novel process for producing hydroxydiphenyl ethers.

Hydroxydiphenyl ethers are useful as materials for synthetic polymers such as wholly aromatic polyesters or various organic chemicals, and various methods for production thereof have been proposed in the past. None, however, have proved to be entirely satisfactory. These known methods may be exemplified as follows with regard to specific reactions.

(1) A method for producing p,p'-dihydroxydiphenyl ether, which comprises reacting p-methoxyphenol sodium salt with p-methoxybromobenzene in the presence of a copper catalyst to form p,p'-dimethoxydiphenyl ether, and subjecting it to ether cleavage [Monatsh., 57, 31–44 (1931)].

(2) A method for producing p,p'-dihydroxydiphenyl ether, which comprises treating p,p'-dibromodiphenyl ether with an aqueous alkali solution in the presence of a copper halide catalyst (U.S. Pat. No. 3,290,386).

(3) A method for directly synthesizing p,p'-dihydroxydiphenyl ether which comprises heating hydroquinone together with hydrogen fluoride (U.S. Pat. NO. 2,739,171).

(4) A method for directly synthesizing p,p'-dihydroxydiphenyl ether from hydroquinone using aluminum silicate as a catalyst (U.S. Pat. No. 3,886,218).

(5) A method for producing p,p'-dihydroxydiphenyl ether, which comprises dehydrocondensing p-isopropylphenol in the presence of a $ThO_2$ catalyst to form p,p'-diisopropyldiphenyl ether (DE-OS 1810179), oxidizing it to dihydroperoxide, and then subjecting it to acid cleavage (U.S. Pat. No. 4,326,088).

The methods (1) and (2) have the defect that the raw materials are difficult to obtain, and the yield of the desired product is low. The method (3) has the defect that the yield of the desired product is low, and toxic hydrogen fluoride must be used. The method (4) is disadvantageous in regard to the yield of the desired product. The method (5) gives a high yield, but is disadvantageous in that the process steps are long, unwanted acetone is formed as a by-product, and treatment of the waste liquor is a problem.

Furthermore, (6) a method for producing p,p'-dihydroxydiphenyl ether from hydroquinone using a strong acid-type ion exchange resin as a catalyst (U.S. Pat. No. 4,306,094), and (7) a method for producing p,p'-dihydroxydiphenyl ether from hydroquinone using H-montmorillonite as a catalyst (U.S. Pat. No. 3,886,218) are known as methods which are simple and give relatively high yields. Industrially, however, these methods are neither satisfactory in yield.

Very recently, Ikawa et al. reported that a certain kind of a metal ion exchanged product of fluoro-tetrasilicic mica is effective as a catalyst for the formation of methyl formate by dehydrogenation of methanol, and with some kind of the metal of the metal ion-exchanged product, the selectivity of the dehydration reaction to dimethyl ether is high [see Chemistry Letters, 1667–1670 (1982)]. They, however, are quite silent on the applicability of this catalyst to other alcohols and hydroxy aromatic compounds.

The present inventors made extensive investigations on a process for producing hydroxydiphenyl ethers, which is free from the aforesaid defects and gives the products in high yields by a simple operation. These investigations have led to the discovery that hydroxydiphenyl ethers can be produced in good yields by a simple operation with reduced side-reaction if the reaction is carried out in the presence of a synthetic mica catalyst in which a specific proportion of interlayer cations is composed of a specific cation.

According to this invention, there is provided a process for producing hydroxydiphenyl ethers, which comprises reacting at least one hydroquinone compound with itself or with a monohydric phenol compound in the presence of a catalyst composed essentially of a synthetic mica in which at least 10 mole% of cation-exchangeable interlayer cations are made up of a metal ion other than alkali metal ions, and/or a proton.

The synthetic mica constituting the catalyst used in this invention is one in which at least 10 mole%, preferably 30 to 100 mole%, of cation-exchangeable interlayer cations are composed of a metal ion other than alkali metal ions, and/or a proton.

The synthetic mica is generally an inorganic layered mineral substance having silicon oxide as a main component. Silicons are connected in a sheet-like form with a hexagonal network structure consisting of $SiO_4$ regular tetrahedrons as a base, and a multiplicity of such sheet-like layers are laid. Among these layers are present interlayer ions, for example metal cations such as alkaline earth metal ions optionally substituted partly or wholly by a proton, an aluminum ion, and at least one cation selected from ions of transition metals.

In the present invention, fluorine-containing synthetic micas (synthetic fluoromicas) are suitably used. In particular, synthetic fluoromicas represented by the following composition formula $$X_p Y_q Z_r Si_{(4-r)} O_{10} F_2 \quad (I)$$

wherein

X is at least one cation having a coordination number of 12,

Y is at least one cation having a coordination number of 6,

Z is at least one cation having a coordination number of 4 excepting $Si^{4+}$, p is a number of from 1/3 to 1, q is a number of from 2 to 3, and r is a number of from 0 to 1, are preferred.

In formula (I), the cation X having a coordination number of 12 includes alkali metal ions and alkaline earth metal ions. Specific examples are $Na^+$, $K^+$, $Ca^{2+}$, $Ba^{2+}$, $Rb^{2+}$, $Cs^{2+}$ and $Sr^{2+}$. Examples of the cation Y having a coordination number of 6 include $Mg^{2+}$, $Fe^{2+}$, $Ni^{2+}$, $Mn^{2+}$, $Al^{3+}$, $Fe^{3+}$ and $Cr^{3+}$. Examples of the cation Z having a coordination number of 4 include $Al^{3+}$, $Ge^{4+}$, $Fe^{3+}$ and $B^{3+}$. $Al^{3+}$ or $Fe^{3+}$ can be both in sixfold and fourfold coordination with the anions, but it should be understood that in formula (I), Y and Z do not represent the same metal ion.

Specific examples of such synthetic fluoromicas are shown below.

Fluorophlogopite $[XMg_{2.5}(AlSi_3O_{10})]F_2$ (X is K)

Tetrasilicic mica $XMg_{2.5}(Si_4O_{10})F_2$ (X is K, Na or Li)

Taeniolite $XMg_2Li(Si_4O_{10})F_2$

Hectorite $X_{1/3}Mg_{2-2/3}Li_{1/3}(Si_4O_4)F_2$ (X is Na or Li)

Of these, tetrasilicic mica and taeniolite can be especially advantageously used in view of their good catalytic performance.

In the synthetic mica used as a catalyst in this invention, at least 10 mole%, preferably 20 to 100 mole%, more preferably 30 to 90 mole%, of the cation-exchangeable interlayer cations in the mica are composed of a metal ion other than alkali metal ions, and/or a proton. Accordingly, when at least 90 mole% of the cation-exchangeable interlayer cations in the synthetic mica are composed of alkali metal ions, it is necessary to exchange the alkali metal ions with another metal ion and/or a proton. On the other hand, if the synthetic mica contains a metal ion other than alkali metal ions, and/or a proton constituting at least 10 mole% of its cation-exchangeable interlayer cations, the mica can be used directly. Needless to say, such a synthetic mica may also be cation-exchanged to increase the proportion of the other metal ion and/or the proton.

The term "cation-exchangeable interlayer cations", as used herein, denotes cations which are present between layers of the synthetic mica used in this invention and are cation-exchangeable as are ordinary ion exchange resins.

Examples of the metal ions other than alkali metal ions, which account for at least 10 mole% of the total amount of the cation-exchangeable interlayer cations of the synthetic mica, include metal ions of Group III-A of the periodic table such as aluminum, gallium and indium, and ions of transition metals such as titanium, zirconium, hafnium, vanadium, niobium, tantalum, chromium, molybdenum, tungsten, manganese, rhenium, iron, ruthenium, cobalt, rhodium, nickel, palladium, copper, gold, zinc, and cadmium. In view of catalytic activity, aluminum, gallium, indium, titanium, zirconium and iron ions are preferred. A proton is also one of preferred cations.

A cation-exchange method known per se can be used to ion-exchange the interlayer ions of the synthetic mica with metal ions and/or a proton. For example, ion-exchange with such metal ions as ions of aluminum and transition metals, can be effected by adding an aqueous solution of a water-soluble salt of such a metal, for example its sulfate, nitrate or chloride, to a suspension of the synthetic mica. More specifically, ion-exchange of Na-type tetrasilicic mica (tetrasilicic mica of the above formula in which X is Na) or Na-type taeniolite (taeniolite of the above formula in which X is Na) will be described as an example. This may be effected by a method which comprises adding an aqueous solution of aluminum sulfate, aluminum nitrate or aluminum chloride to a suspension of the Na-type tetrasilicic fluoromica or Na-type taeniolite preferably purified so that the amount of the aluminum ion added is about 0.5 to about 5 gram ion equivalents, preferably about 0.8 to about 2 gram ion equivalents, per gram ion equivalent of the Na ion to be exchanged, stirring the mixture at room temperature for about 2 to about 60 minutes or allowing the mixture to stand, separating the solid layer by filtration or centrifugal separation, thereafter washing it with water and/or ethanol, and drying it at room temperature to about 100° C. under reduced pressure or atmospheric pressure. As required, this ion-exchange treatment may be repeated a plurality of times.

Usually, the cation-exchanged synthetic mica is in the form of a powder. In the present invention, it may be used directly as a catalyst. As required, it may be molded into a tablet, a spherical or cylindrical tablet, or a ring-like shape, or a honeycomb shape together with a suitable binder such as diatomaceous earth, silica gel, alumina, clay, magnesia, talc.

In these synthetic mica catalysts, cation-exchanged metal ions are uniformly dispersed in the layer, and almost all of them contribute to the high performance of the catalyst. Furthermore, since the catalyst composed of the synthetic mica can be prepared by a simple operation, it is quite suitable as a catalyst for the dehydrocondensation reaction of a hydroquinone compound with itself or with a monohydric phenolic compound.

For use in the reaction of the hydroquinone compound with itself or with the monohydric phenolic compound, the amount of the synthetic mica catalyst used is not critical, and can be varied widely according to the types of the starting materials, the reaction conditions, etc. Conveniently, the amount of the synthetic mica used is generally 1 to 50% by weight, preferably 5 to 40% by weight, more preferably 5 to 20% by weight, based on the weight of the hydroquinone compound.

The "hydroquinone compound" to be reacted in the presence of the synthetic mica catalyst in accordance with this invention is hydroquinone optionally having at least one substituent on the benzene ring, and preferably includes those of the following formula

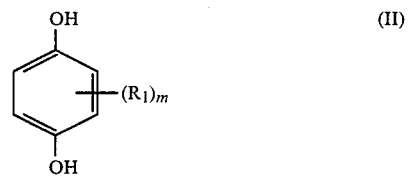 (II)

wherein $R_1$ represents a halogen atom or a lower alkyl group, m is an integer of 0 to 4, preferably 0 to 2, provided that when m is at least 2, the $R_1$ groups may be identical or different.

Specific examples include hydroquinone, methylhydroquinone, 2,5-dimethylhydroquinone, 2,6-dimethylhydroquinone, trimethylhydroquinone, ethylhydroquinone, isopropylhydroquinone, n-hexylhydroquinone, chlorohydroquinone, 2,6-dichlorohydroquinone and bromohydroquinone.

The term "lower", as used herein to qualify a group or a compound, means that the group or compound so qualified has not more than 6, preferably not more than 3, carbon atoms.

The "monohydric phenol compound" to be reacted with the hydroquinone compound, is phenol optionally having at least one substituent on the benzene ring, and preferably includes those of the following formula

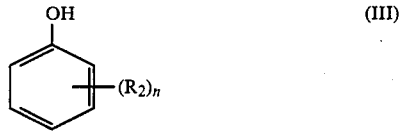 (III)

wherein $R_2$ represents a lower alkyl group, an aryl group (e.g., a phenyl group), an aralkyl group (e.g., a benzyl group), a lower alkoxy group, a halogen atom, a nitro group, an acyl group (especially, a lower alkanoyl group), or an aroyl group (e.g., a benzoyl group), n represents an integer of 0 to 5, particularly 0 to 4, provided that when n is 2 or more, the $R_2$ groups may be identical or different.

Specific examples include phenol, o-cresol, m-cresol, p-cresol, 3,4-xylenol, 3,5-xylenol, 2,4-xylenol, 3,4,5-trimethylphenol, p-n-propylphenol, p-n-hexylphenol, p-benzylphenol, m-benzylphenol, p-phenylphenol, m-phenylphenol, p-(p'-tolyl)phenol, p-chlorophenol, m-chlorophenol, p-bromophenol, m-bromophenol, 2,4-dichlorophenol, p-methoxyphenol, m-methoxyphenol, m-nitrophenol, p-nitrophenol, m-methoxyphenol, p-methoxyphenol, p-acetylphenol, m-acetylphenol and p-benzoylphenol.

According to this invention, the hydroquinone compound may be used singly and reacted with itself. Thus, when the hydroquinone compound of formula (II) alone is used as a starting material, a p,p'-dihydroxydiphenyl ether of the following formula

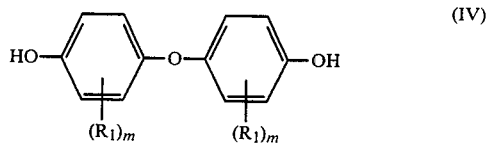

wherein $R_1$ and m are as defined above, is formed in a high conversion and a high selectivity with scarcely any formation of by-products.

According to another embodiment of this invention, the hydroquinone compound is reacted with the monohydric phenol compound. When the hydroquinone of formula (II) and the monohydric phenol compound of formula (III) are used as starting materials, a hydroxydiphenyl ether of the following formula

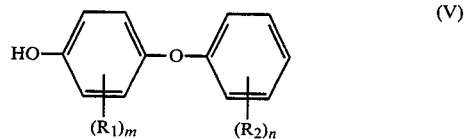

wherein $R_1$, $R_2$, m and n are as defined above, can be formed in a high yield. It is surprising that in this reaction in the presence of the synthetic mica catalyst in accordance with this invention, there is virtually no formation of a diphenyl ether which is a condensation product of the monohydric phenol compound. Accordingly, this is advantageous in increasing the yield of the monohydroxydiphenyl ether of formula (V). In this reaction, the condensation reaction of the hydroquinone compound with itself can occur. But if the monohydric phenol compound is used in a large molar excess with respect to the hydroquinone compound, the monohydroxydiphenyl ether of formula (V) can be selectively formed while inhibiting the condensation reaction of the hydroquinone compound with itself.

The aforesaid reactions in accordance with this invention can be carried out in various embodiments. Desirably, these reactions are carried out in the liquid phase. Usually, these reactions are carried out preferably in the presence of a solvent, although the use of solvent may be obviated. Examples of the solvent which can be used at this time include substituted or unsubstituted aromatic hydrocarbons such as benzene, toluene, xylene, ethylbenzene, mesitylene, chlorobenzene, dichlorobenzene, bromobenzene, biphenyl, and terphenyl; aromatic ethers such as diphenyl ether, benzofuran and dibenzofuran; and aromatic ketones such as acetophenone and benzophenone. Of these, alkylbenzenes such as toluene, xylene and mesitylene are preferred.

The amount of the solvent used is usually such that the concentration of the starting compounds in the reaction mixture is 2 to 80% by weight, preferably 5 to 20% by weight.

The reaction temperature is usually about 80 to about 200° C., preferably about 90° to about 185° C., especially preferably about 110° to about 170° C.

The reaction can be carried out by heating a mixture of the synthetic mica catalyst, the solvent and the starting materials to a predetermined temperature exemplified above. The heating time is usually from about 10 minutes to about 6 hours, preferably from about 30 minutes to about 2 hours. Various modes of the reaction can be employed including a batchwise process or a continuous process in a tubular reactor.

The reaction may be carried out under reduced, atmospheric or elevated pressure. Furthermore, since the reaction in accordance with this reaction is a dehydration reaction, water is formed as the reaction proceeds. The reaction, therefore, proceeds more easily if it is carried out while removing the water from the reaction system in a customary manner.

After the reaction, the reaction mixture is subjected to a general separating procedure such as distillation or chromatography with or without prior removal of the catalyst. As a result, the desired hydroxydiphenyl ether can be obtained easily. Very small amounts of hydroxytriphenyl ether and hydroxytetraphenyl ether may form as by-products in the reaction product in addition to the hydroxydiphenyl ether. These by-products can be easily separated by distillation, etc.

According to the method of this invention described above, hydroxydiphenyl ethers can be produced easily in good yields by the condensation reaction of the hydroquinone alone, or the reaction of the hydroquinone compound with the monohydric phenol compound.

The following examples illustrate the present invention more specifically. These examples should not be construed as limiting the present invention.

EXAMPLE 1

One hundred grams of a 10% by weight aqueous solution of sodium tetrasilicic mica (synthetic mica produced by Topy Kogyo K.K.) was suspended in 1 liter of water, and with good stirring, 200 ml of a 5% aqueous solution of Al $(NO_3)_3$ was used. The mixture was further stirred for 25 minutes to cation-exchange it to an aluminum type. The synthetic mica of the aluminum type was recovered by centrifugal separation, well washed with water, and dried at 40° C. and 50 mmHg for 10 hours for use in the following reaction. The cation exchange ratio of the aluminum cation-exchanged synthetic mica was 72 mole%.

A mixture of 8.0g of the aluminum cationexchanged synthetic mica, 25g of hydroquinone, and 150 ml of mesitylene was put in a reactor equipped with a Dean-Stark water-collecting trap. The mixture was heated with stirring for 3 hours under refluxing of mesitylene while removing the formed water out of the reactor as an azeotrope with mesitylene. Thus, dehydrodimerization of hydroquinone was carried out. The results of the reaction were as follows:

TABLE 1

| | |
|---|---|
| Hydroquinone conversion | 84.2% |
| Selectivity * to 4,4'- | 92.6% |

TABLE 1-continued

| | |
|---|---|
| dihydroxydiphenyl ether | |
| Trimer and other oligomers | 7.4% |

*: Based on the reacted hydroquinone.

EXAMPLE 2

One hundred grams of a 10% by weight aqueous solution of sodium tetrasilicic mica (synthetic mica made by Topy Kogyo K.K.) was suspended in 1 liter of water, and with good stirring, 185g of an about 5% aqueous solution of $Ti(SO_4)_2$ was added to form a titanium ion-exchanged synthetic mica.

Hydroquinone was dehydrodimerized in the same way as in Example 1 except that the resulting titanium ion-exchanged synthetic mica was used. The results are shown in Table 2.

TABLE 2

| | |
|---|---|
| Conversion of hydroquinone | 58.5% |
| Selectivity * to 4,4'-dihydroxydiphenyl ether | 91.5% |
| Trimer and other oligomers | 8.5% |

*: Based on the reacted hydroquinone.

EXAMPLE 3

Monomethylhydroquinone was dehydrodimerized in the same way as in Example 1 except that monomethylhydroquinone was used instead of hydroquinone. The results are shown in Table 3.

TABLE 3

| | |
|---|---|
| Conversion of monomethylhydroquinone | 68.0% |
| Selectivity * to 4,4'-dihydroxy-3,3'-dimethylhydroquinone | 55.6% |
| Selectivity * to 4,4'-dihydroxy-2,3'-dimethylhydroquinone | 30.7% |
| Selectivity * to 4,4'-dihydroxy-2,2'-dimethylhydroquinone | 5.7% |

EXAMPLE 4

Hydroquinone was reacted with phenol using the same aluminum cation-exchanged synthetic mica as used in Example 1. Specifically, 5.0g of the aluminum cation-exchanged synthetic mica, 15.0g of hydroquinone, 190g of phenol and 200 ml of mesitylene were reacted by the same method as in Example 1. The results are shown in Table 4.

TABLE 4

| | |
|---|---|
| Conversion of hydroquinone | 66% |
| Selectivity * to 4-hydroxy-diphenyl ether | 78% |
| Selectivity * to 4,4'-dihydroxydiphenyl ether | 21% |
| Diphenyl ether | trace |

*: Based on the reacted hydroquinone.

EXAMPLE 5

Hydroquinone (21g) and 170g of p-cresol were reacted in the presence of 7 g of the same aluminum cation-exchanged synthetic mica as used in Example 1. The results are shown in Table 5.

TABLE 5

| | |
|---|---|
| Conversion of hydroquinone | 86% |
| Selectivity * to 4-hydroxy-4'-methyldiphenyl ether | 81% |
| Selectivity * to 4,4'-dihydroxyhydroquinone | 14% |
| Selectivity * to 4,4'-dimethyldiphenyl ether | trace |

*: Based on the reacted hydroquinone.

EXAMPLE 6

Hydroquinone (13g) and 212g of p-chlorophenol were reacted for 6 hours in the presence of diphenyl ether using 4 g of the same aluminum cation-exchanged synthetic mica as used in Example 1. The results are shown in Table 6.

TABLE 6

| | |
|---|---|
| Conversion of hydroquinone | 54% |
| Selectivity* to 4-hydroquinone-4'-chlorodiphenyl ether | 54% |
| Selectivity* to 4,4'-dihydroxydiphenyl ether | 38% |

*: Based on the reacted hydroquinone.

EXAMPLE 7

One hundred grams of a 10% by weight aqueous solution of sodium tetrasilicic mica (synthetic mica made by Topy Kogyo K.K.) was suspended in 1 liter of water, and with good stirring, 200 ml of an about 5% aqueous solution of $Ga(NO_3)_3$ was added. The product was recovered in the same way as in Example 1 to obtain a gallium cation-exchanged synthetic mica. The ion exchange ratio was 62%.

Hydroquinone was dehydrodimerized in the same way as in Example 1 except that the resulting gallium cation-exchanged synthetic mica was used. The results are shown in Table 7.

TABLE 7

| | |
|---|---|
| Conversion of hydroquinone | 62.1% |
| Selectivity to 4,4-dihydroxydiphenyl ether | 90.3% |
| Trimer and other oligomers | 9.7% |

EXAMPLE 8

One hundred grams of a 10% by weight aqueous solution of sodium tetrasilicic mica (synthetic mica made by Topy Kogyo K.K.) was suspended in 1 liter of water, and with good stirring, 200 ml of an about 5% aqueous solution of $In_2(SO_4)_3$ was added. The product was recovered in the same way as in Example 1 to prepare an indium cation-exchanged synthetic mica. The ion exchange ratio was 57%.

Hydroquinone was dehydrodimerized in the same way as in Example 1 except that the resulting In cation-exchanged synthetic mica was used. The results are shown in Table 8.

TABLE 8

| | |
|---|---|
| Conversion of hydroquinone | 55.3% |
| Selectivity to 4,4-dihydroxy-diphenyl ether | 91.8% |
| Trimer and other oligomers | 8.2% |

EXAMPLE 9

One hundred grams of a 10% by weight aqueous solution of sodium tetrasilicic mica (synthetic mica made by Topy-Kogyo K.K.) was suspended in 1 liter of water, and with good stirring, 200 ml of an about 5% aqueous solution of Fe(NO$_3$)$_3$ was added. The product was recovered in the same way as in Example 1 to obtain an iron cation-exchanged synthetic mica. The ion exchange ratio was 73%.

Hydroquinone was dehydrodimerized in the same way as in Example 1 except that the resulting iron cation-exchanged synthetic mica was used. The results are shown in Table 9.

TABLE 9

| | |
|---|---|
| Conversion of hydroquinone | 54.7% |
| Selectivity to 4,4-dihydroxy-diphenyl ether | 92.1% |
| Trimer and other oligomers | 7.9% |

EXAMPLE 10

One hundred grams of a 10% by weight aqueous solution of sodium tetrasilicic mica (synthetic mica made by Topy Kogyo K.K.) was suspended in 1 liter of water, and with good stirring, 200 ml of an about 5% aqueous solution of Zr(SO$_4$)$_2$ was added. The product was recovered in the same way as in Example 1 to obtain a zirconium cation-exchanged synthetic mica. The cation exchange ratio was 55%.

Hydroquinone was dehydrodimerized in the same way as in Example 1 except that the resulting zirconium cation-exchanged synthetic mica was used. The results are shown in Table 10.

TABLE 10

| | |
|---|---|
| Conversion of hydroquinone | 42.6% |
| Selectivity to 4,4-dihydroxy-diphenyl ether | 93.8% |
| Trimer and other oligomers | 6.2% |

What is claimed is:

1. A process for producing a hydroxydiphenyl ether, which comprises reacting at least one hydroquinone compound with itself or with a monohydric phenol compound at a temperature of about 80° C. to about 200° C. while removing the formed water in the presence of a solvent and a catalyst composed essentially of a synthetic mica in which at least 10 mole% of cation-exchangeable interlayer cations are made up of at least one metal ion selected from metal ions of Group III-A of the periodic table and transition metal ions, or of said metal ion and a proton.

2. The process of claim 1 wherein from 30 to 100 mole% of the cation-exchangeable interlayer cations of the synthetic mica are made up of said at least one metal ion.

3. The process of claim 2 wherein said at least one metal ion is selected from the group consisting of an aluminum ion, a titanium ion, an indium ion, an iron ion, a gallium ion, a zirconium ion and mixtures thereof with a proton.

4. The process of claim 1 wherein the synthetic mica is a synthetic fluoromica of the type represented by the following composition formula $$X_p Y_q Z_r Si_{(4-r)} O_{10} F_2 \quad (I)$$

wherein
X is at least one cation having a coordination number of 12,
Y is at least one cation having a coordination number of 6,
Z is at least one cation having a coordination number of 4 other than Si$^{4+}$,
p is a number of from 1/3 to 1,
q is a number of from 2 to 3, and
r is a number of from 0 to 1.

5. The process of claim 1 wherein the synthetic mica is derived from fluoromica, tetrasilicic mica, taeniolite or hectorite.

6. The process of claim 1 wherein the synthetic mica is derived from tetrasilicic mica or taeniolite.

7. The process of claim 1 wherein the synthetic mica is used in an amount of from 1 to 50% by weight, based on the weight of the hydroquinone compound.

8. The process of claim 1 for producing a p, p'-dihydroxydiphenyl ether of the following formula (IV):

$$HO-\underset{(R_1)_m}{\underset{|}{\bigcirc}}-O-\underset{(R_1)_m}{\underset{|}{\bigcirc}}-OH \quad (IV)$$

wherein
R$_1$ is a halogen atom or a lower alkyl group,
m is an integer of 0 to 4, provided that when m is at least 2, the R$_1$ groups may be identical or different,
which comprises reacting the hydroquinone compound of the following formula (II)

$$\underset{OH}{\underset{|}{\bigcirc}}-(R_1)_m \quad (II)$$
$$OH$$

wherein R$_1$ and m are as defined above, with itself.

9. The process of claim 1 for producing a hydroxydiphenyl ether of the following formula (V)

$$HO-\underset{(R_1)_m}{\underset{|}{\bigcirc}}-O-\underset{(R_2)_n}{\underset{|}{\bigcirc}} \quad (V)$$

wherein
R$_1$ is a halogen atom or a lower alkyl group, R$_2$ is a lower alkyl group, an aryl group, an aralkyl group, a lower alkoxy group, a halogen atom, a nitro group, an acyl group, or an aroyl group, m is an integer of 0 to 4 and n is an integer of 0 to 5, provided that when m is at least 2, the R$_1$ groups may be identical or different and when n is 2 or more, the R$_2$ groups may be identical or different,
which comprises reacting a hydroquinone compound of the following formula (II)

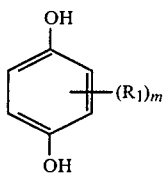

(II)

wherein

R₁ and m are as defined above, with a monohydric phenol compound of formula (III)

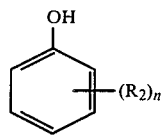

(III)

wherein

R₂ and n are as defined above.

10. The process of claim 9 wherein the monohydric phenol compound of formula (III) is used in a molar excess with respect to the hydroquinone-compound of formula (II).

11. The process of claim 1 wherein the solvent is used in an amount such that the concentration of the reactants in the reaction mixture is 2 to 80% by weight.

* * * * *